(12) United States Patent
Niu

(10) Patent No.: US 10,252,271 B2
(45) Date of Patent: Apr. 9, 2019

(54) METHODS AND APPARATUS FOR GENERATING DROPLETS

(71) Applicant: University of Southampton, Southampton (GB)

(72) Inventor: Xize Niu, London (GB)

(73) Assignee: University of Southampton, Southampton, Hampshire (GB)

( * ) Notice: Subject to any disclaimer, the term of this patent is extended or adjusted under 35 U.S.C. 154(b) by 112 days.

(21) Appl. No.: 15/306,996

(22) PCT Filed: Apr. 30, 2015

(86) PCT No.: PCT/GB2015/051258
§ 371 (c)(1),
(2) Date: Oct. 26, 2016

(87) PCT Pub. No.: WO2015/166248
PCT Pub. Date: Nov. 5, 2015

(65) Prior Publication Data
US 2017/0050187 A1 Feb. 23, 2017

(30) Foreign Application Priority Data

Apr. 30, 2014 (GB) .................. 1407602.0

(51) Int. Cl.
*B01L 3/00* (2006.01)
*G01N 30/32* (2006.01)
(Continued)

(52) U.S. Cl.
CPC ..... *B01L 3/502784* (2013.01); *B01L 3/50273* (2013.01); *B01L 3/502715* (2013.01);
(Continued)

(58) Field of Classification Search
CPC ....... B01L 2300/0867; B01L 2300/123; B01L 2200/028; B01L 2200/0684;
(Continued)

(56) References Cited

U.S. PATENT DOCUMENTS 3,935,971 A  2/1976  Papoff et al.
4,673,334 A * 6/1987  Allington ............ F04B 43/1292
                                                                417/475
(Continued)

FOREIGN PATENT DOCUMENTS

CN   1500002   5/2004
CN   101827709   9/2010
(Continued)

OTHER PUBLICATIONS

State Intellectual Property Office of the People's Republic of China (SIPO), First Notification of Office Action (dated Jan. 31, 2018), with English Translation (19 pages).
(Continued)

*Primary Examiner* — Jennifer Wecker
(74) *Attorney, Agent, or Firm* — Cook Alex Ltd.

(57) ABSTRACT

Methods and apparatus for generating droplets are disclosed. In one arrangement a peristaltic screw pump is configured to drive pulsatile flows of fluids in different conduits which are phased relative to each other such that a sequence of droplets are formed at a junction downstream from the pump.

20 Claims, 8 Drawing Sheets

(51) Int. Cl.
*F16K 11/00* (2006.01)
*F04B 43/12* (2006.01)
*F04B 19/00* (2006.01)
*B01L 9/00* (2006.01)
*C12M 3/06* (2006.01)
*F16K 11/16* (2006.01)
*F04B 43/04* (2006.01)

(52) U.S. Cl.
CPC ...... *B01L 3/502738* (2013.01); *F04B 19/006* (2013.01); *F04B 43/12* (2013.01); *G01N 30/32* (2013.01); *B01L 9/527* (2013.01); *B01L 2200/0673* (2013.01); *B01L 2200/0684* (2013.01); *B01L 2200/10* (2013.01); *B01L 2200/18* (2013.01); *B01L 2300/0816* (2013.01); *B01L 2300/0819* (2013.01); *B01L 2300/0867* (2013.01); *B01L 2300/0883* (2013.01); *B01L 2300/123* (2013.01); *B01L 2400/0481* (2013.01); *B01L 2400/0644* (2013.01); *C12M 23/16* (2013.01); *F04B 43/043* (2013.01); *F04B 43/1269* (2013.01); *F16K 11/163* (2013.01); *G01N 2030/326* (2013.01)

(58) Field of Classification Search
CPC ............. B01L 2200/10; B01L 2200/18; B01L 2300/0816; B01L 2300/0819; B01L 2300/0864; B01L 2300/12; B01L 2400/0481; B01L 2400/0644; B01L 2400/0655; B01L 3/502715; B01L 3/50273; B01L 3/502738; B01L 9/527; B01L 2200/0673; B01L 2300/0883; B01L 3/502784; F04B 43/12; F04B 43/043; F04B 43/1269; F04B 43/1292; F04B 19/006; C12M 21/08; C12M 23/16; C12M 23/44; C12M 23/52; C12M 29/00; C12M 29/10; C12M 29/20; F16K 11/163; G01N 2030/326; G01N 30/32
See application file for complete search history.

(56) References Cited

U.S. PATENT DOCUMENTS

| | | | | |
|---|---|---|---|---|
| 5,257,917 A * | 11/1993 | Minarik | ............... | F04B 43/1292 417/475 |
| 2003/0026719 A1* | 2/2003 | Hahn | .................... | F04B 43/043 417/476 |
| 2007/0242111 A1 | 10/2007 | Pamula et al. | | |
| 2009/0214366 A1 | 8/2009 | Shener | | |
| 2010/0285975 A1 | 11/2010 | Mathies et al. | | |
| 2012/0015428 A1* | 1/2012 | Seale | ................ | B01L 3/502707 435/283.1 |
| 2013/0240073 A1* | 9/2013 | Xia | ...................... | G05D 7/0113 137/843 |
| 2013/0287613 A1* | 10/2013 | Gould | ................. | F04B 43/1269 417/476 |
| 2014/0319237 A1 | 10/2014 | Brothier et al. | | |
| 2015/0174576 A1* | 6/2015 | Van Vilet | .............. | B01L 3/0241 506/12 |
| 2015/0238959 A1* | 8/2015 | Prakash | ............ | B01L 3/502738 506/7 |

FOREIGN PATENT DOCUMENTS

| | | |
|---|---|---|
| CN | 103249493 | 8/2013 |
| WO | WO02/056988 | 7/2002 |
| WO | WO2009/028947 | 3/2009 |
| WO | WO 2010/118150 | 10/2010 |
| WO | WO 2012/048261 | 4/2012 |
| WO | WO 2014/001781 | 1/2014 |
| WO | WO 2014/039844 | 3/2014 |

OTHER PUBLICATIONS

International Search Report, counterpart International Appl. No. PCT/GB2015/051258 (dated Jul. 27, 2015) (4 pages).

Written Opinion of the International Searching Authority, counterpart International Appl. No. PCT/GB2015/051258 (dated Jul. 27, 2015) (8 pages).

Thorsen, Todd et al., Dynamic Pattern Formation in a Vesicle-Generating Microfluidic Device, Physical Review Letters, vol. 86, No. 18, 4163-4166 (Apr. 30, 2001).

Anna, Shelley L. et al., Formation of Dispersions Using "Flow Focusing" in Microchannels, Applied Physics Letters, vol. 82, No. 3, 364-366 (Jan. 20, 2003).

* cited by examiner

METHODS AND APPARATUS FOR GENERATING DROPLETS

The present invention relates to methods and apparatus for generating droplets, particularly droplets of an aqueous phase dispersed in a continuous and immiscible oil phase or droplets of an oil phase dispersed in a continuous and immiscible aqueous phase. The invention is particularly applicable to generating microdroplets having a size range in the nanoliter to picoliter range. The droplets may be used for chemical and biological reactions or other analyses.

Apparatus for producing such droplets are well known. Smaller droplets are sometimes referred to as "microdroplets". Various microfluidic structures for generating the droplets and/or for transporting them after generation are known.

Microdroplets have become a reliable tool for performing biological operations such as encapsulation, sampling, metering, dilution and detection. Microdroplets in microfluidics offer a great number of opportunities in chemical and biological research and applications. They provide a compartment in which species or reactions can be isolated, they are monodisperse and therefore suitable for quantitative studies, they offer the possibility to work with extremely small volumes, single cells, or single molecules, and are suitable for high-throughput experiments.

Droplet generation is one of the most important steps in droplet microfluidics, especially when sampling low volume or low concentration samples. Various approaches are known. So-called passive systems may involve bringing together the different fluids for forming the droplets at a conduit junction (e.g. a T-junction), resulting in a stream of droplets downstream of the junction. Alternatively, flow focusing geometries may be used to bring fluids of different composition together and generate or focus droplets in order to form a stream of droplets downstream of a focusing region. Typically, syringe pumps are used to pump the fluids through these geometries in microfluidic chips. However, syringe pumps require relatively large samples, are bulky, and cannot be used for sampling from biological (e.g. tissue) environments directly. Other pumping systems are known (e.g. piezoelectric pumps, compressed air pumps, compressed air controlled interdigital pumps in PDMS chips, etc.), but such arrangements also tend to be complex and/or bulky, making them unsuitable for portable units, continuous operation, and/or expensive. Furthermore, in many arrangements the pumping action is necessarily initiated at a considerable distance from where the droplets are formed and/or used, which can lead to problems controlling droplet size (the droplets can end up being polydispersed with different volumes or the flow rate needs a long time to be stabilized). It can also be difficult to control generation frequency accurately using such methods. So-called active systems are also known, which may involve the use of time-dependent perturbations of the fluid flow (using for example electric fields, pneumatic pressure, magnetic fields, acoustic waves or optical fields). These systems may allow good control of the droplet size and generation frequency without varying channel geometries or volumetric flow rates, but can be expensive and generally exhibit lower droplet-generation rates.

It is an object of the invention to provide methods and apparatus that address one or more of the problems with the prior art discussed above.

According to an aspect of the invention, there is provided an apparatus for generating droplets, comprising: a first conduit for transporting a first fluid; a second conduit for transporting a second fluid; and a pumping mechanism comprising a first rotatable member having one or more radially peripheral portions that engage against the first and second conduits and apply a dynamic deformation to the first and second conduits on rotation of the first rotatable member, the dynamic deformation being such as to drive a pulsatile motion of the first and second fluids in the first and second conduits, wherein the pulsatile motions of the first and second fluids are phase shifted relative to each other at a first junction between the first and second conduits downstream of the pumping mechanism resulting in the formation of droplets of the second fluid in the first fluid at the first junction.

Thus, an apparatus of simple and inexpensive construction is provided that can reliably and accurately form droplets of stable, fixed size. For each revolution of the rotatable member, the pumping mechanism (comprising for example a screw thread) will pump fixed amounts of fluids into the conduits. By arranging for conduits to be placed at different positions around the circumference of the rotatable member (e.g. on opposite sides), the flows can be arranged to be at least partially out of phase (i.e. phase shifted by a finite phase angle, optionally but not essentially 180 degrees) at a junction, which allows fluid (the second fluid) from one conduit reliably to form droplets within the fluid (the first fluid) in another conduit. The flows in the first and second conduits may be such that one stream starts to flow while the other stops, and vice versa, for example.

In an embodiment, one droplet is produced per revolution of the rotatable member. In the case where the first rotatable member comprises a screw thread the droplet volume will be fixed by the screw pitch and the shape and dimensions of the second conduit, and is relatively insensitive to the rotational frequency and overall speed of flow. This means that the speed of flow can easily be changed without necessarily changing the droplet volume. Indeed, in typical embodiments, flow rate can be changed from relatively low (e.g. one droplet per minute or hour) to relatively high (e.g. several or tens of droplets per minute) while maintaining droplet size uniformity to within about 3%.

The principle can be applied to produce droplets for example with diameters in the range of less than a few microns (e.g. 1 micron) to a few millimeters (e.g. 5 or 10 mm).

The apparatus allows the sample (the second fluid) to be compartmentalised into droplets directly adjacent to the pump mechanism (or in very close proximity thereto). This is not possible in many prior art arrangements, for example in prior art systems for continuous fluidic based sampling like microdialysis. It is known in such systems that Taylor dispersion in the collection tubing and related signal smearing is a significant problem. In the present invention such effects can be greatly reduced by forming the droplets directly adjacent to the pump mechanism.

The time and frequency of droplet generation can be adjusted with ease. For example where the rotatable member is driven by an electrical motor it is merely necessary to control the motor's frequency or on-off Droplets can be generated at a rate of a few droplets per second or one in several minutes, for example. The technique is therefore highly flexible and can be used to produce droplets on-demand (e.g. a predetermined number at a time, in response to individual requests).

A single rotatable member can drive fluids through three or more different conduits simultaneously, making it possible easily to add to the droplets a variety of different chemical reagents, for example for labelling or reactions, or even to add in a third or more phases into the flow stream; for example a gas can be pumped in to form gas bubbles, for example within an oil/aqueous phase and/or to coexist with the sample droplets.

In an embodiment, the first rotatable member comprises a thread winding around its axis. The thread may provide a continuous seal against backflow of material, thereby effectively separating the sample environment, where the pressure would typically be lower, from the conduits downstream of the first rotatable member (e.g. comprising conduits formed in a microfluidic chip), where pressure is typically higher. Therefore the droplet generation and subsequent manipulation of the droplets does not affect the physiological environment (e.g. in the tissue). Crucially, carrier fluid, e.g. oil, and/or the other reagents are always confined by the thread away from the sampling probe (e.g. microdialysis probe, ultrafiltration probe, push-pull probe, etc.), and there is no risk of contamination or electric contact to the sample (especially body or tissue).

Furthermore, in contrast to prior art arrangements, the pumping mechanism of the disclosed embodiments does not create any dead volumes. All fluid that enters the pump mechanism is driven reliably through the pump mechanism.

In an embodiment the pumping mechanism is configured to operate as a peristaltic pump.

In an embodiment, a plurality of rotatable members are provided that have radially peripheral portions having different characteristics. The plurality of rotatable members can be driven to rotate simultaneously and make it possible to achieve a variety of different effects. Conduits can be provided that have different cross-sectional areas and/or shapes. Droplets having different sizes, spacings and/or streams having different flow rates can be generated simultaneously for example.

Droplets may be formed at different positions along the first conduit by the provision of multiple junctions at which droplets are formed. This allows droplets of different composition to be formed in parallel, allowing more complex sequences of droplets to be formed reliably and efficiently.

In an embodiment, longitudinal axes of conduits are non-parallel to the axis of rotation of the first rotatable member in a region where the radially peripheral portions engage against the conduits. In such an embodiment plural sets of radially peripheral portions may be provided, optionally having different spacings, angular offsets and/or geometries to allow a range of different effects to be achieved.

In an embodiment, a conduit support structure comprises a lumen defining the first conduit and a lumen defining the second conduit. Optionally, the conduit support structure is continuously integral along at least one path from the lumen defining the first conduit to the lumen defining the second conduit. The conduit support structure allows the conduits (e.g. first and second conduits) to be provided in a single structure, facilitating ease of manufacture and/or handling after manufacture. The conduit support structure also helps to ensure that conduits reliably maintain a desired spatial relationship relative to each other. The conduit support structure allows the conduits to be formed in a particularly compact manner because the conduit support structure simultaneous defines the conduits and provides a mounting for the conduits. Complex pathways for conduits can easily be manufactured, including conduits that cross over each other and/or otherwise form plural layers in the radial direction.

According to an alternative aspect of the invention, there is provided a method of generating droplets, comprising: using a pumping mechanism to transport a first fluid in a first conduit; and using the pumping mechanism to transport a second fluid in a second conduit, wherein the pumping mechanism comprises a first rotatable member having one or more radially peripheral portions that engage against the first and second conduits and apply a dynamic deformation to the first and second conduits on rotation of the first rotatable member, the dynamic deformation being such as to drive a pulsatile motion of the first and second fluids in the first and second conduits, and the pulsatile motions of the first and second fluids are phase shifted relative to each other at a junction between the first and second conduits downstream of the pumping mechanism resulting in the formation of droplets of the second fluid in the first fluid at the junction.

Embodiments of the invention will now be described, by way of example only, with reference to the accompanying drawings in which corresponding reference symbols indicate corresponding parts, and in which.

Figure 13:
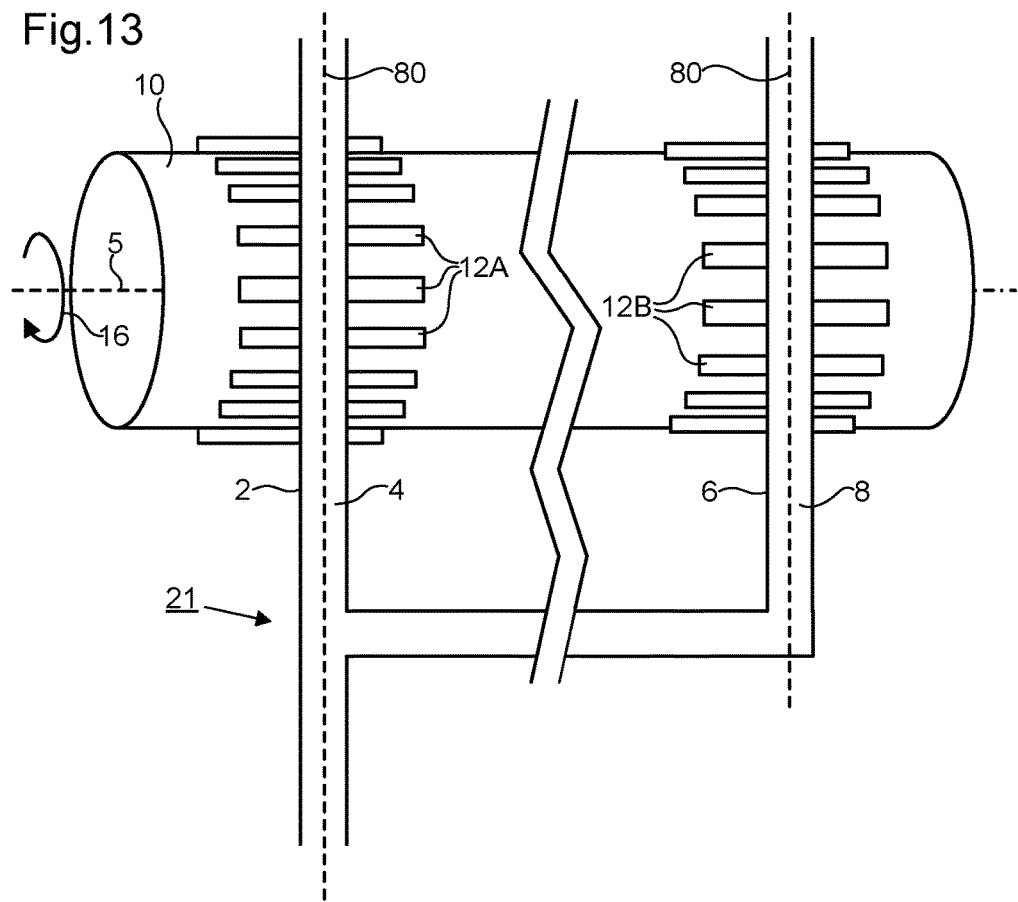
FIG. 13 is a schematic perspective view of an apparatus for generating droplets in which longitudinal axes of conduits are perpendicular to an axis of rotation of a first rotatable member.
Figure 16:
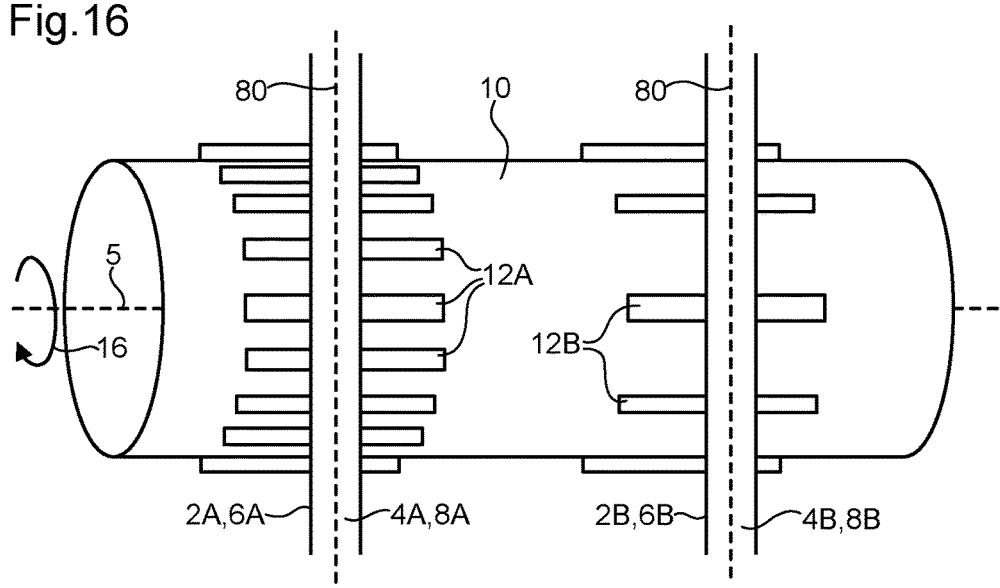
Figure 17:
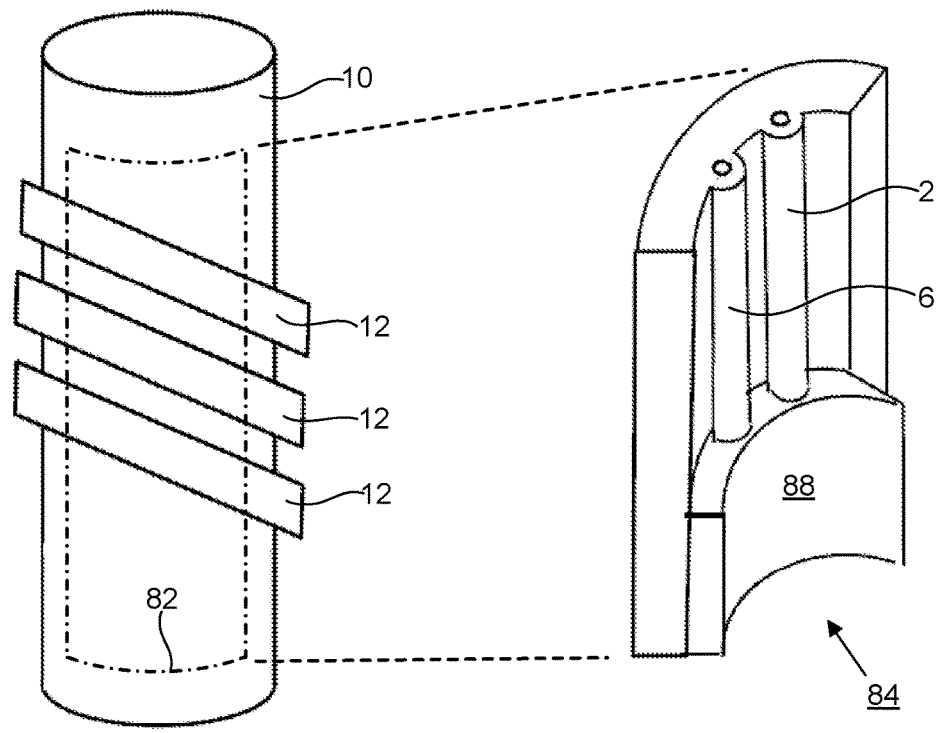

FIG. 16 is a schematic perspective view of an apparatus for generating droplets of the type shown in FIG. 13 except that the first and second sets of radially peripheral portions are configured simultaneously to impart pulsatile motions of different frequency; and FIG. 17 shows schematic perspective views of 1) a rotatable member (left) and 2) a cut-out portion of a conduit support structure (right) configured to engage against the rotatable member shown on the left.

In the following, where reference is made to a "fluid" this is understood to encompass at least a liquid or a gas.

Figure 1:
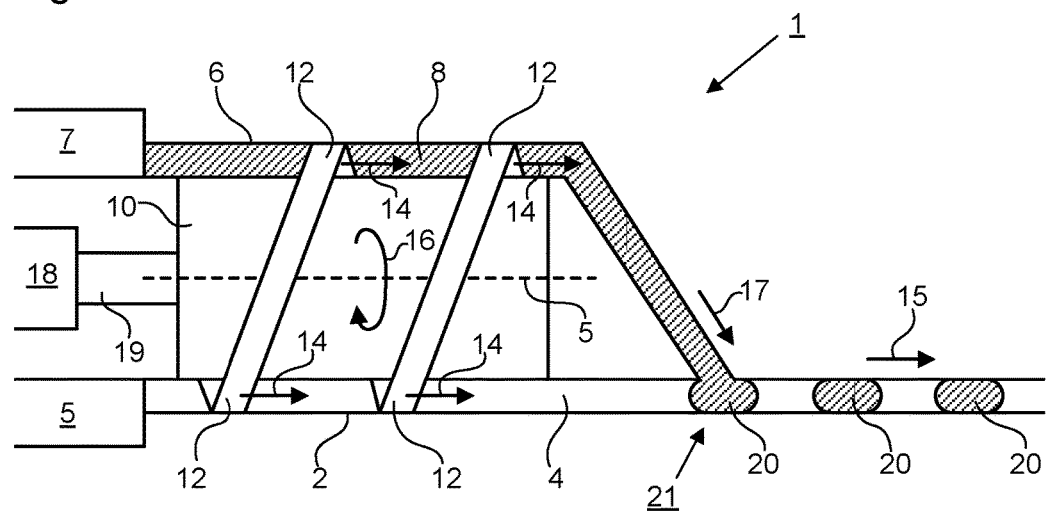
FIG. 1 is a schematic side view of an apparatus for generating droplets according to an embodiment.

FIG. 1 depicts an apparatus 1 for generating droplets 20. The apparatus 1 comprises a first conduit 2 for transporting a first fluid 4. The apparatus 1 further comprises a second conduit 6 for transporting a second fluid 8. In other embodiments one or more further conduits may be provided for transporting one or more further fluids.

A pumping mechanism is provided for pumping the fluids along the conduits. The pumping mechanism comprises a first rotatable member 10 having one or more radially peripheral portions 12. In the present embodiment, the one or more radially peripheral portions 12 are formed from a single thread running around a longitudinal axis 5 of the rotatable member 10, for example in a helical path. The peripheral portions 12 engage against the first and second conduits 2 and 6 and are configured to apply a dynamic deformation to the first and second conduits 2 and 6 on rotation 16 of the first rotatable member 10 about the axis 5. The conduits 2 and 6 may be formed from a flexible material, for example in the form of a cylindrical tube, that can withstand repeated deformations without failure. The dynamic deformation may comprise squeezing of the conduits, optionally so that the conduits are substantially sealed longitudinally at the point of squeezing. The point of squeezing may move along the conduit as the rotatable member 10 rotates, for example in the form of a moving ripple. The movement of the point of squeezing is an example of the dynamic nature of a dynamic deformation. However, other forms of dynamic (i.e. time varying) deformations may also be used.

The dynamic deformation drives a corresponding pulsatile motion of the first and second fluids 4 and 8 in the conduits. The pulsatile motion may be such that at any given longitudinal position in the conduit, downstream of the pumping mechanism, the average fluid velocity as a function of time is periodic and/or resembles a series of pulses. The average fluid velocity is therefore relative high at the peaks of the pulses and much lower in between the pulses (optionally at or near zero). The pumping mechanism may operate on the principle of a peristaltic pump. In this particular configuration, where the radially peripheral portions 12 comprise a thread, the pumping mechanism may be referred to as a screw pump mechanism or a peristaltic screw pump mechanism.

Rotation of the rotatable member 10 may be driven for example by an electric motor 18 via drive shaft 19. The first fluid may be provided to the first conduit 2 by a reservoir 5 (or by other means). The second fluid may be provided to the second conduit 6 by a reservoir 7 (or by other means). Either or both of these reservoirs may be detachable from the corresponding conduits.

The second fluid 8 is driven 17 by the pumping mechanism into the first fluid 4 at a junction 21 between the first and second conduits 2 and 6, downstream of the pumping mechanism. The junction 21 may be referred to as a "first junction" because one or more further junctions may optionally be provided (as described below). The pulsatile motions of the first and second fluids 4 and 8 are phase shifted relative to each other at the junction 21, resulting in the formation of well defined droplets of the second fluid 8 in the first fluid 4 at the junction 21. The size of the droplets and the spacing between the droplets remains substantially uniform regardless of the speed of rotation of the rotatable member over a wide range of speeds of rotation.

Figure 2:
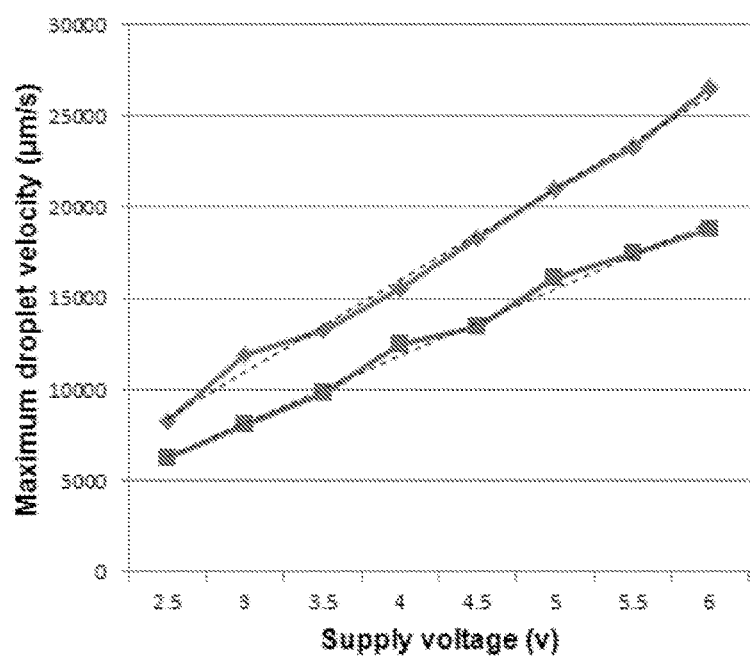
FIG. 2 is an experimental graph showing droplet velocity against supply voltage to a pump motor.
Figure 3:
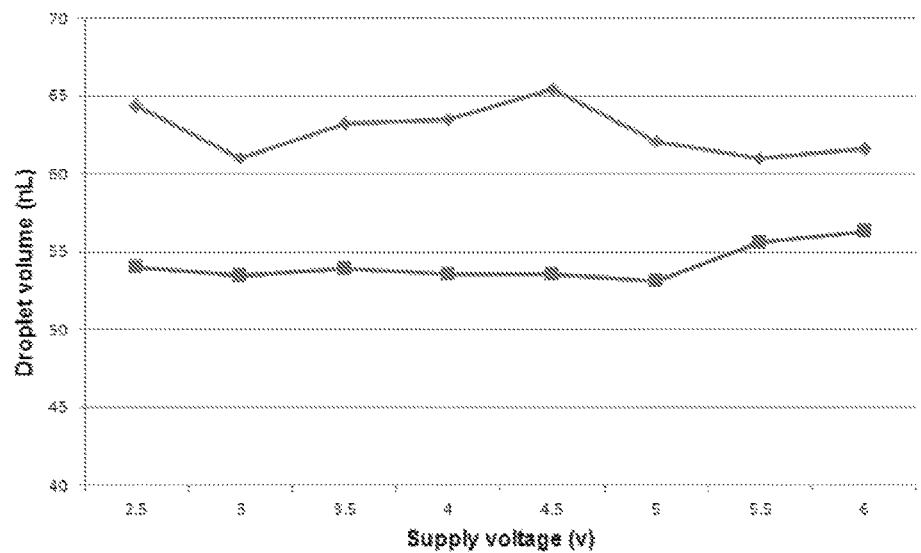
FIG. 3 is an experimental graph showing droplet volume against supply voltage to a pump motor.

The inventors performed test measurements on the pumping mechanism, example results of which are shown in FIGS. 2 and 3. FIG. 2 shows how the droplet velocity (proportional to the total flow rate because the droplet volume remains constant) increases linearly with the increase of rotation speed of the pumping mechanism (indicated by increasing supply voltage to the electric motor 18). FIG. 3 shows how the droplet sizes are near constant for different flow rates and droplet generation frequencies. In these tests, FC-40 oil was used as the first fluid (an oil phase in this example) and water mixed with red food dye was used as the second fluid (an aqueous phase in this example). Many other different combinations of first and second fluid compositions may be used. Uniform droplet generation was verified by high speed video recording and subsequent analysis of the resulting videos. Test measurements demonstrated that the droplet generation frequency/sampling frequency can be varied easily from relatively low (e.g. one sample/droplet per minute or hour) to relatively high (several or tens of droplets per second). Over this range the droplets generated had a uniform size within about 3%.

Figure 4:
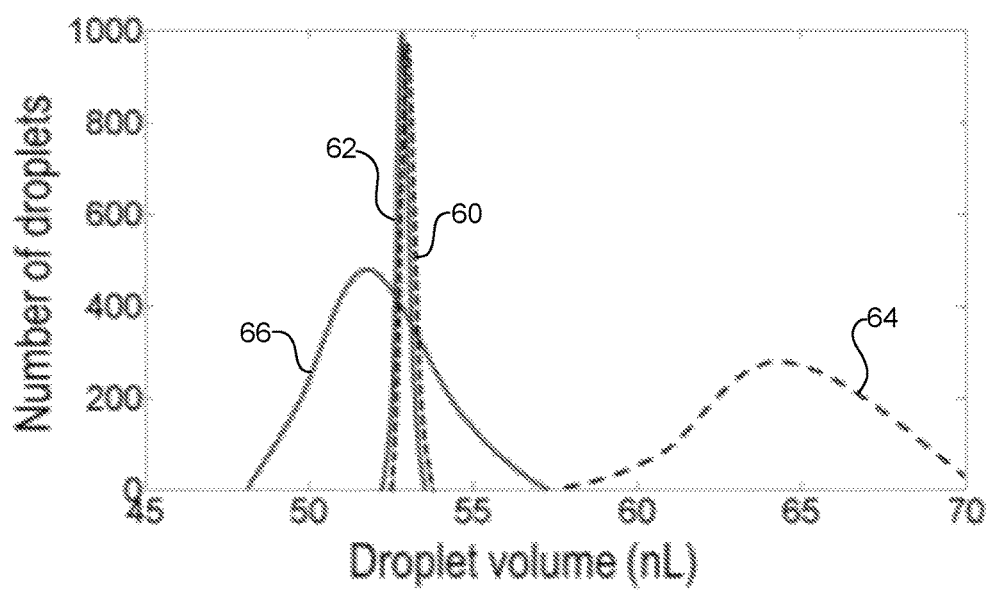
FIG. 4 shows an experimental histogram graph comparing droplets generated by an apparatus for generating droplets according to an embodiment with droplets generated using a typical prior art syringe pump.

FIG. 4 shows further experimental results in the form of a histogram plot comparing droplets generated experimentally by the inventors using an apparatus for generating droplets according to an embodiment compared with a typical prior art syringe pump. The embodiment is of a type in which the one or more radially peripheral portions 12 comprises a thread winding around the axis of the first rotatable member 10. Embodiments of this type may be referred to as "screw pumps". The vertical axis measures the number of droplets. The horizontal axis measures the droplet volume. Broken line 60 shows results for the screw pump for a first flow rate Q1 (=0.9 μL/min). Solid line 62 shows results for the same screw pump for a second flow rate Q2 (=1.4 μL/min). Broken line 64 shows results for the syringe pump for the first flow rate Q1. Solid line 66 shows results for the same syringe pump for the second flow rate Q2.

As can be seen, the screw pump generates droplets of more uniform size for a given flow rate (narrower peak), relative to the syringe pump. Furthermore, the variation in droplet size with flow rate is much smaller for the screw pump than for the syringe pump (the curves 60 and 62 are substantially aligned with each other along the horizontal axis whereas the curves 64 and 66 are well separated from each other along the horizontal axis).

In an embodiment, longitudinal axes of the first and second conduits 2 and 6 (e.g. axes parallel to a direction of elongation of the conduits and to an average direction of flow through the conduits) are parallel to the axis of rotation 5 of the first rotatable member 10 in a region where the one or more radially peripheral portions 12 engage against the first and second conduits 2 and 6. This is the case for example in the arrangement depicted in FIG. 1, but may also be the case in any other arrangement where this would be compatible.

In an embodiment, the one or more radially peripheral portions 12 comprises a thread winding around the axis 5 of the first rotatable member 10. This is the case for example in the arrangement depicted in FIG. 1, but may also be the case in any other arrangement where this would be compatible.

Figure 5:
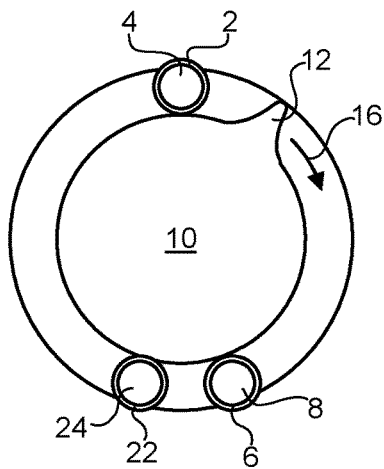
FIG. 5 is a schematic end sectional view of an apparatus for generating droplets according to an embodiment comprising three conduits engaging with a rotatable member.

In an embodiment, the apparatus 1 comprises one or more further conduits 22. A schematic end sectional view of such an embodiment is depicted in FIG. 5. Each of the further conduits 22 is configured such that the one or more radially peripheral portions 12 engage against each of the one or more further conduits 22 and apply a dynamic deformation to each of the one or more further conduits 22 on rotation of the first rotatable member 10. The dynamic deformation drives a corresponding pulsatile motion of fluid 24 in each of the one or more further conduits 22. In an embodiment, the one or more further conduits 22 are configured such that fluid in these conduits 22 can be driven into the first fluid 4 at the junction 21 between the first and second conduits 2 and 6 in order to form droplets 20 in the first fluid 4 that comprise a mixture of the second fluid 8 and fluid 24 from the one or more further conduits 22. The fluid 24 may comprise one or more chemical reagents for example, to assist with testing of the fluid 8.

In the example shown in FIG. 5, only a single further conduit 22 is shown, but in other embodiments, two, three or more further conduits may be provided, each providing the possibility of adding one or more further components to the droplets 20. In general each of the conduits with which a given rotatable member engages will be positioned at a different angular position around the circumference of the rotatable member 10.

Figure 6:
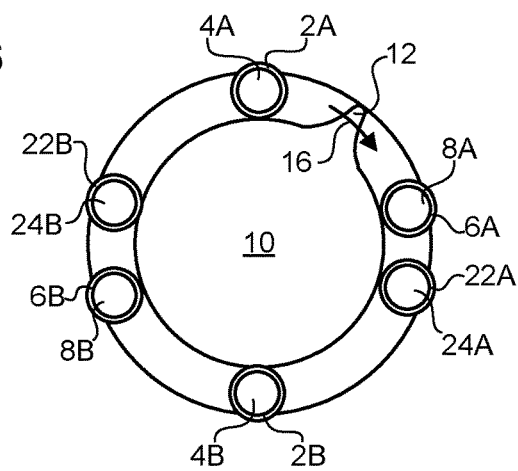
FIG. 6 is a schematic end sectional view of an apparatus for generating a sequence of droplets of different composition in series.
Figure 7:
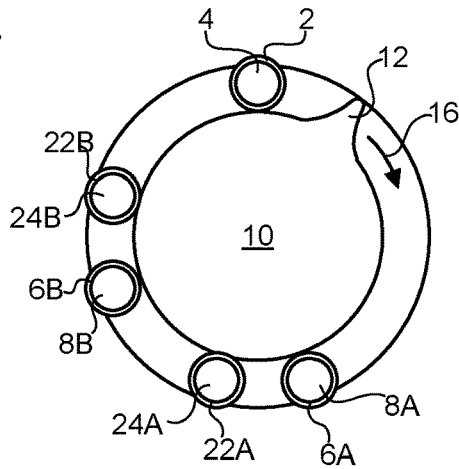
FIG. 7 is a schematic end sectional view of an apparatus for generating droplets of different composition in parallel.
Figure 8:
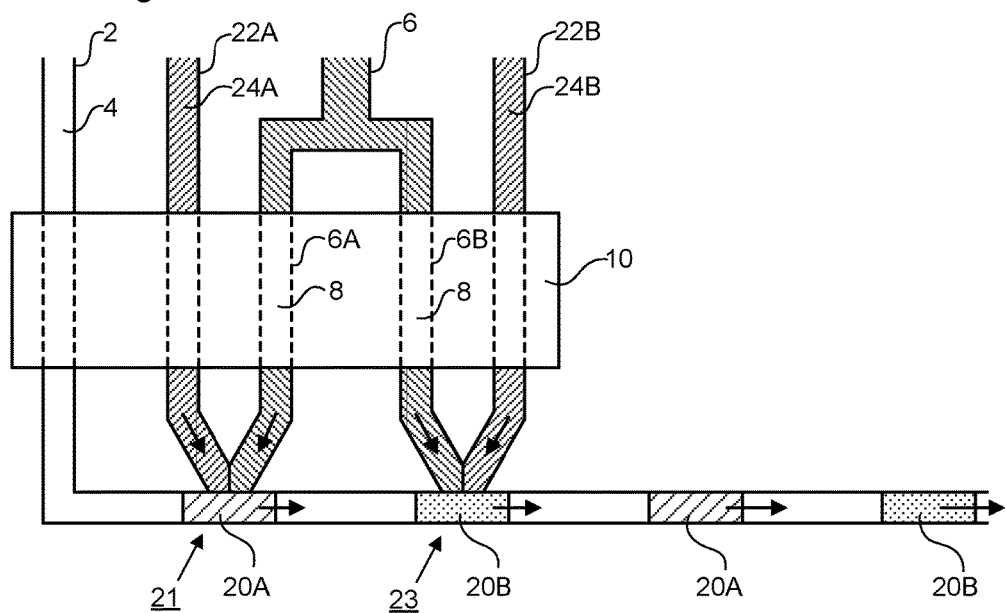
FIG. 8 depicts a schematic side view of the apparatus of FIG. 7.

In an embodiment, a sequence of droplets having different compositions may be formed in an output conduit. This can be achieved in series or in parallel. FIG. 6 depicts an example configuration for series generation. FIGS. 7 and 8 depict an example configuration for parallel generation.

FIG. 6 is a schematic end sectional view of a configuration that is the same as that of FIG. 5 except that a further three conduits are provided that are phase shifted by 90 degrees relative to the three conduits of FIG. 5 (90 degrees is just an example; other phase shifts may be used instead). Thus, instead of a single first conduit 2, two first conduits 2A and 2B are provided. These may alternatively be referred to as a single first conduit 2A and a further conduit 2B. Instead of a single second conduit 6, two second conduits 6A and 6B are provided. These may alternatively be referred to as a single second conduit 6A and a further conduit 6B. Instead of a single further conduit 22, two further conduits 22A and 22B are provided. In this embodiment all of the conduits lead to a single first junction 21 (not shown). A pulse of carrier fluid 4A is pumped via first conduit 2A followed by the injection of a first droplet comprising sample fluid 8A and reagents 24A via conduits 6A and 22A, followed by a further pulse of a carrier fluid 4B via first conduit 2B, followed by the injection of a second droplet comprising sample fluid 8B and reagents 24B via conduits 6B and 22B. The process then repeats to generate in series a sequence of alternating first and second droplets leaving the junction 21. The conduits 2A and 2B carrying the carrier fluid 4A and 4B may carry the same carrier fluid. The conduits 2A and 2B may be joined together downstream from the pumping mechanism but upstream from the junction 21 at which the droplets are formed.

FIGS. 7 and 8 depict schematic end sectional and side views respectively of an example of a type of embodiment in which two separation junctions with the first conduit 2 are provided: a first junction 21 and a second junction 23. In such an embodiment at least one of the one or more further conduits 22B is configured such that fluid 24B in the conduit 22B can be driven into the first fluid 4 at the second junction 23. Thus, droplets can be formed in parallel. In the example shown, the second conduit 6 is branched into two branches 6A and 6B, each respectively carrying second fluid 8 (e.g. sample fluid) to the first and second junctions 21 and 23. In the particular example shown, a further conduit 22A carries a further component (e.g. a reagent) 24A to the first junction 21 and a further conduit 22B carries a further component (e.g. a reagent) 24B to the second junction 23. Thus, two different types of droplet 20A and 20B can conveniently and efficiently be produced in parallel in the same output conduit. The same sample (second fluid 8) can be formed into droplets having different reagents added thereto in the same droplet stream, thereby providing a droplet stream that can allow multiple different tests to be applied to the sample in a convenient manner. Various other arrangements are possible, including having three of more junctions with the first conduit and fewer or more than one further conduits 22 leading to one or more of the junctions. It is not essential for the same second fluid (sample) to be injected at all of the junctions 21 and 23. In other embodiments, different second fluids (samples) may be injected at two or more different junctions.

Figure 9:
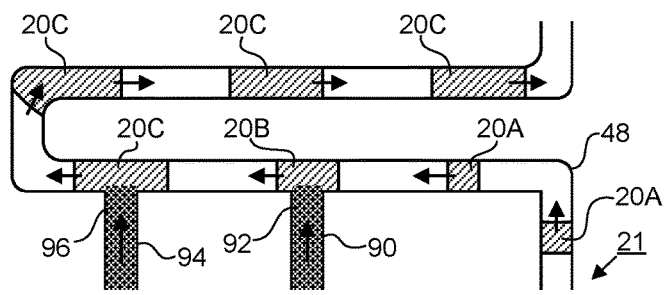
FIG. 9 depicts addition of supplementary compositions to droplets after droplet generation in a labyrinthine output conduit.

In the embodiments described above reagents or other components to be added to a sample droplet 20 are added at the junction (e.g. first junction 21 and/or second junction 23) where the droplet is formed. However, this is not essential. In other embodiments, reagents or other components can be added to droplets downstream of the junction at which they are formed. This process is illustrated schematically in FIG. 9. Here, a labyrinthine output conduit 48 is provided downstream of a junction 21 at which droplets 20A of a sample are formed. Auxiliary conduits 90 and 94 respectively add components 92 and 96 to the droplets as they pass. Thus, droplet 20B is formed at auxiliary conduit 90 by addition of component 92 to droplet 20A. Droplet 20C is formed at auxiliary conduit 94 by addition of component 96 to the droplet 20B. The components 92 and 96 in auxiliary conduits 90 and 94 will need to be pumped at a timing that is appropriate for injecting the components 92 and 96 when the droplets are in the appropriate positions. This can be achieved using a pumping mechanism according to an embodiment of the present invention or by using another type of pumping mechanism. The well defined and consistent nature of the droplets 20A (e.g. consistent droplet length, size and/or separation) formed by the pumping mechanism according to embodiments of the present invention helps to ensure that reagents or other components added to droplets downstream of the junction 21 at which the droplets are initially formed are added reliably and consistently.

The said first fluid may comprise a carrier fluid and the said second fluid may comprise a sample fluid, the sample fluid being immiscible with the carrier fluid. Optionally, the carrier fluid is a hydrophobic or oleophilic fluid and the sample fluid is an aqueous fluid. For example, the sample fluid may comprise biological material, for example taken from a human or animal body. In other embodiments the carrier fluid may be an aqueous fluid and the sample may be a hydrophobic or oleophilic fluid. Other combinations of immiscible liquids or gases may be used.

In an embodiment the apparatus 1 is configured for use in a context where at least one of the conduits is intended to be brought into contact with a patient being treated or assessed. In this situation it is important to be able to maintain sterility. The pumping mechanism of the present invention is advantageous in this context because no element of the pump needs to be in direct contact with the fluids in the conduits. The pumping action is achieved purely by imparting the dynamic deformation to the conduits. Furthermore, the peristaltic action can be configured to provide an effective seal against backflow of material. For example, radially peripheral portions 12 may be provided that engage with the conduit in question in such a way that for all angles of rotation of the rotatable member the conduit is sealed at least one longitudinal position.

Figure 10:
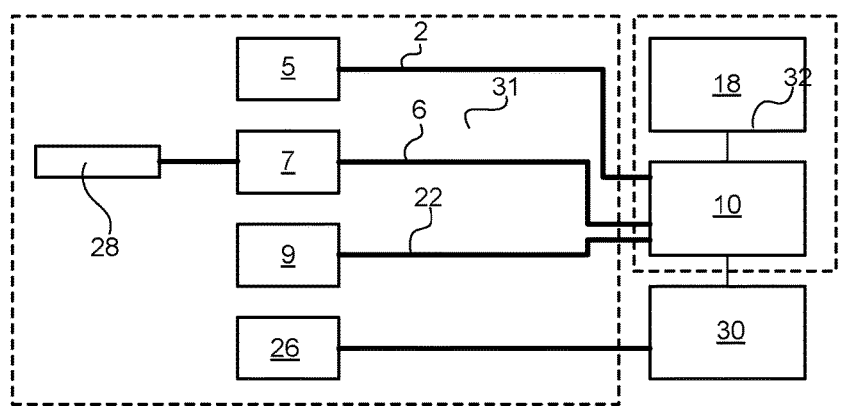
FIG. 10 is a schematic block diagram showing connections between elements of an apparatus for generating droplets according to an embodiment.

Additional advantages can be obtained by providing the apparatus 1 in modular form. For example, the apparatus 1 may be divided into parts which need to be sterile and parts which do not need to be sterile. The parts that need to be sterile may be detached from the apparatus 1 and replaced by new parts or replaced after undergoing a sterilization program. Parts which do not need to be sterile may be reused. FIG. 10 illustrates one way the apparatus of FIG. 5 might be formed in such a modular fashion.

The rotatable member 10 and motor 18 do not need to be sterile and may therefore be formed as a single unit 32 which is detachable from the other components of the apparatus 1. Alternatively, the rotatable member 10 and motor 18 may be formed as two separate elements that are detachable from each other as well as from other components of the apparatus 1. The conduits 2, 6 and 22 and/or corresponding reservoirs 5, 7 and 9 may be provided as a single unit 31 that is replaced between different uses of the apparatus 1. Thus, one or more of the conduits are detachably connected to the pumping mechanism to allow reuse of the pumping mechanism with different sets of conduits.

The apparatus 1 may further comprise a sampling probe 28 for collecting fluid to be tested. The sampling probe 28 may be inserted into the patient being treated for example. The sampling probe 28 may provide fluid to the reservoir 7 (as shown) or directly to the second conduit 6. The sampling probe 28 may be provided as part of the unit 31 (as shown) or as a separate element.

The apparatus 1 may further comprise a detector 30 configured to test droplets output from the pumping mechanism (i.e. downstream of the junction 21 at which the droplets 20 are formed). The droplets may be tested optically or electrochemically, or according to any other of the various techniques known in the art for testing droplets of biological material. The detector 30 may be formed as part of one of the two units 31 and 32 or as separate unit (as shown).

Figure 11:
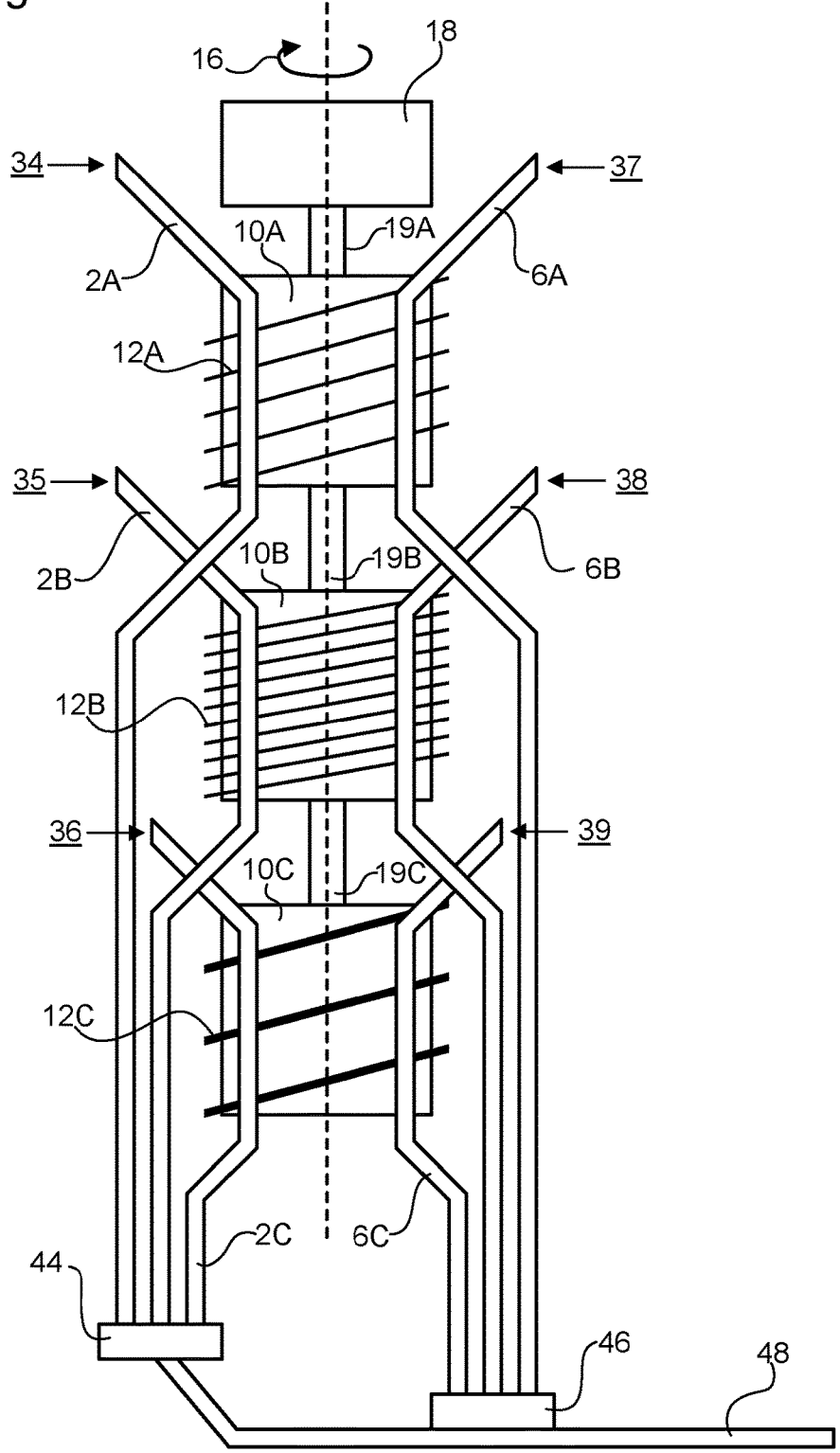
FIG. 11 is a schematic side view of an apparatus for generating droplets that comprises three rotatable members according to an embodiment.

In an embodiment, the pumping mechanism comprises one or more further rotatable members configured to be rotated in unison with the first rotatable member 10. An example of such an embodiment is depicted in FIG. 11. Here, three rotatable members 10A-C are provided, each connected together rigidly by connecting elements 19A-C. Each of the rotatable members 10A-C comprises one or more radially peripheral portions (shown schematically by slanted elements 12A-C) that engage against corresponding first and second conduits 2A-C and 6A-C. The one or more radially peripheral portions 12A-C apply a dynamic deformation to the conduits 2A-C and 6A-C with which they engage on rotation of the rotatable member 10A-C. The dynamic deformation drives a corresponding pulsatile motion of fluid in the conduits 2A-C and 6A-C.

In an embodiment, each of the rotatable members 10A-C is configured to apply a dynamic deformation having a different form (causing for example a pulsatile fluid motion in the conduits that has a different wavelength). For example, the dynamic deformation applied by one of the further rotatable members 10A-C may be such as to cause formation of droplets having a different size in comparison with droplets formed by the dynamic deformation applied by another one of the rotatable members 10A-C for the same speed of rotation and shape of conduits transporting the fluids forming the droplets. This may be achieved for example by arranging for the dynamic deformations applied by the two rotatable members concerned to have different periods for the same speed of rotation. Where the radially peripheral portions 12 comprise screw threads for example, the number of windings per unit length may be arranged to be different.

Regardless of whether a single rotatable member 10 or multiple rotatable members 10A-C is/are provided, the separation between the droplets and the size of the droplets can also be varied by changing the relative cross-sectional areas of the conduits. For example, increasing the cross-sectional area of conduits carrying a carrier fluid will tend to increase the separation between droplets and vice versa. Similarly, increasing the cross-sectional area of conduits carrying the sample fluid and/or reagents to be added to the droplet will tend to increase the volume of the droplets and vice versa.

Thus, for a single given speed of rotation of the rotatable members 10A-C (drivable therefore by a single motor without any complex gearing) it is possible to achieve a stream of droplets having a variety of different properties (e.g. different droplet sizes and/or separations) by selecting different rotatable members 10A-C and/or conduit geometries. The different rotatable members may also provide different flow rates for a given speed of rotation (e.g. reducing the number of windings per unit length will tend to increase the flow rate per unit length).

A plurality of different entry ports 33-39 may be provided to allow access to conduits that engage with different rotatable members 10A-C. Coupling units 44 and 46 provide coupling between the conduits downstream of the rotatable members 10A-C and an output conduit 48. The coupling units may be configured to allow selective connection of one or more of the conduits 2A-C and 6A-C to the output conduit 48 downstream of the rotatable members 10A-C. Droplets are formed at the coupling unit 46.

In the arrangement shown all three of the rotatable members 10A-C are different from each other (i.e. have different radially peripheral portions 12). However, this is not essential. In other embodiments two or more of the multiple rotatable members 10A-C may be the same. This may be advantageous for example because it may make it easier to have a particular type of dynamic deformation applied to a larger number of conduits because space limitations around the circumference of a single rotatable member are no longer the limiting factor. In an embodiment of this type, the coupling unit 46 for example may be configured simultaneously to allow fluid from two or more of the incoming conduits 6A-C from different rotatable members 10A-C to flow into the output conduit 48.

Figure 12:
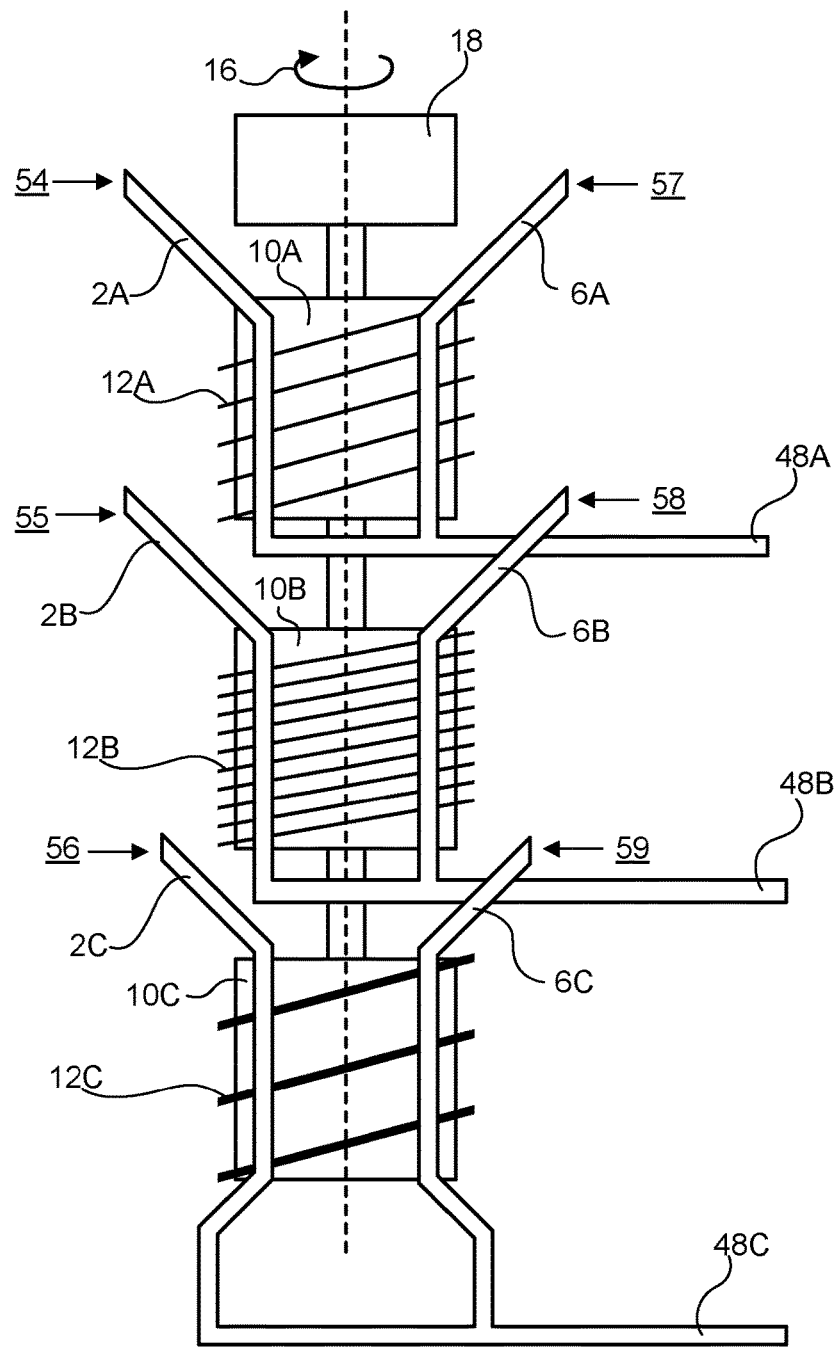
FIG. 12 is a schematic side view of an apparatus for generating droplets that comprises three rotatable members according to an alternative embodiment.

FIG. 12 depicts an alternative embodiment in which three different sets of first and second conduits 2A-C and 6A-C engage with three different rotatable members 10A-C. Downstream of the respective rotatable members 10A-C, each of the three sets of first and second conduits 2A-C and 6A-C join to form a different output conduit 48A-C. Thus, in contrast to the arrangement of FIG. 11, it is possible in the arrangement of FIG. 12 simultaneously to generate streams of droplets having different properties from each other by suitably applying fluid to the plurality of input ports 54-59. A stream of small droplets and a stream of larger droplets could for example be generated simultaneously, optionally via a single sampling probe, and channelled to different testing stations (each requiring for example different volumes of droplet). Alternatively or additionally, streams having different overall flow rates could be provided simultaneously, optionally via a single sampling probe, and channelled to different testing stations (each requiring different flow rates).

In the arrangements shown in FIGS. 10 and 11, only two conduits 2A-C and 6A-C are depicted for each rotatable member 10A-C. However, this is not essential. In other embodiments, more than two conduits may engage with one or more of the rotatable members 10A-C.

In other embodiments, two or more than three of the rotatable members are provided.

In the embodiments discussed above, no further pumping is provided downstream from the junction or junctions at which droplets 22 are formed. However, this is not essential. For example, an output conduit transporting droplets 20 downstream from a junction 21 at which the droplets 20 were formed may be routed so as to engage a second time with the pumping mechanism. For example, the output conduit may be routed such that over a range of positions downstream from the junction 21 the one or more radially peripheral portions 10 engage against the output conduit and apply a dynamic deformation to the output conduit, on rotation of the first rotatable member, thereby further driving a corresponding pulsatile motion of fluid in the output conduit.

In the embodiments discussed above with reference to FIGS. 1-12, examples are shown in which the first and second conduits 2 and 6 (longitudinal axes thereof) are parallel to an axis of rotation 5 of the first rotatable member 10 where they engage with the radially peripheral portions 12. This is not essential. In other embodiments, longitudinal axes of the first and second conduits 2 and 6 are arranged to be non-parallel to the axis of rotation 5 of the first rotatable member 10 where they engage with the radially peripheral portions 12. In particular embodiments, examples of which are shown in FIGS. 13-16, the longitudinal axes of the first and second conduits 2 and 6 are arranged to be perpendicular to the axis of rotation 5 where they engage with the radially peripheral portions 12. The longitudinal axes are the conduits are labelled "80" in FIGS. 13 and 16.

In embodiments where the first and second conduits 2 and 6 are non-parallel to the axis of rotation 5, the radially peripheral portions 12A may engage against the first conduit 2 exclusively within a first range of positions along the axis 5, and the radially peripheral portions 12B may engage against the second conduit 6 exclusively within a second range of positions along the axis 5. The first range of positions is different to the second range of positions. Optionally the first range of positions does not overlap with the second range of positions. This can be seen to be the case in the examples shown in FIGS. 13-16 for example.

In an embodiment, a set of radially peripheral portions 12A that engage against the first conduit 2, which may be referred to as a first set, is different from a set of radially peripheral portions 12B that engage against the second conduit 6, which may be referred to as a second set. Optionally, the first and second sets are mutually exclusive. This is the case in the examples of FIGS. 13-16. Having mutually exclusive sets provides increased freedom for configuring the radially peripheral portions 12A, 12B, thereby increasing flexibility of use.

In the examples shown in FIGS. 13-16, the radially peripheral portions 12A,12B comprise linear ridges. The ridges are parallel to the axis of rotation 5 of the first rotatable member 10. The ridges are spaced apart evenly relative to each other. In other embodiments the ridges may take other forms.

As in the embodiments discussed with reference to FIGS. 1-12, the radially peripheral portions 12A,12B engage against the first and second conduits 2 and 6 and are configured to apply a dynamic deformation to the first and second conduits 2 and 6 on rotation 16 of the first rotatable member 10 about the axis 5. The conduits 2 and 6 may be formed as described above with reference to FIGS. 1-12. The dynamic deformation may be as described above with reference to FIGS. 1-12. The dynamic deformation drives a corresponding pulsatile motion of the first and second fluids 4 and 8 in the conduits. Rotation of the rotatable member 10 may be driven as described above with reference to FIGS. 1-12. The first and/or second fluids may be provided to the first conduit 2 by one or more reservoirs (not shown) or by other means.

As in the embodiments discussed above with reference to FIGS. 1-12, the second fluid 8 may be driven 17 by the pumping mechanism into the first fluid 4 at a junction 21 between the first and second conduits 2 and 6, downstream of the pumping mechanism. The junction 21 may be referred to as a "first junction" because one or more further junctions may optionally be provided (as described above). The pulsatile motions of the first and second fluids 4 and 8 are phase shifted relative to each other at the junction 21, resulting in the formation of well defined droplets of the second fluid 8 in the first fluid 4 at the junction 21. The size of the droplets and the spacing between the droplets remains substantially uniform regardless of the speed of rotation of the rotatable member over a wide range of speeds of rotation.

Figure 14:
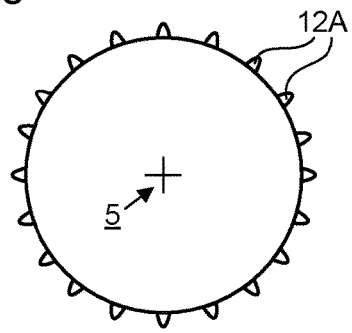
FIG. 14 is a schematic axial sectional view showing angular positions of a first set of radially peripheral portions configured to apply a dynamic deformation to a first conduit in the apparatus of FIG. 13.
Figure 15:
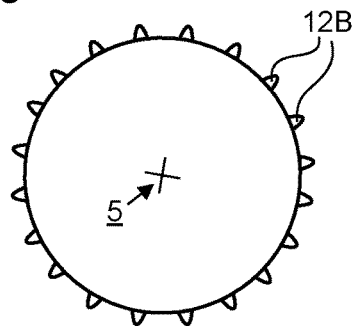
FIG. 15 is a schematic axial sectional view showing angular positions of a second set of radially peripheral portions configured to apply a dynamic deformation to a second conduit in the apparatus of FIG. 13.

In the embodiments described above with reference to FIGS. 1-12, the phase shifting between the pulsatile motions of the first and second fluids 4 and 8 at the junction 21 was provided by positioning the conduits at different angular positions around the circumference of the rotatable member 10. The variation in the position of the radially peripheral portions 12 along the circumferential direction (due for example to the thread/spiral form of the radially peripheral portions 12) provided the phase shifting. In example embodiments where the conduits are non-parallel, for example perpendicular, to the axis of rotation 5 of the rotatable member 10 an alternative approach may be taken. In the example of FIG. 13, the phase shifting is provided by an angular offset between the first and second sets of radially peripheral portions 12A,12B. The angular offset can be seen most clearly in the axial sectional views of FIGS. 14 and 15 (FIG. 14 is a sectional view through the first set and FIG. 15 is a section view through the second set).

FIG. 16 illustrates how different sets of radially peripheral portions 12A, 12B can be configured to apply dynamic deformations having different forms (causing for example pulsatile fluid motions in the conduits that have different wavelengths). For example, the dynamic deformation applied by one of the sets of radially peripheral portions 12A may be such as to cause formation of droplets having a different size in comparison with droplets formed by the dynamic deformation applied by another one of the sets of radially peripheral portions 12B for the same speed of rotation and shape of conduits transporting the fluids forming the droplets. In the example of FIG. 16 this functionality is provided by arranging for the separation between the radially peripheral portions 12A in the first set to be smaller than the separation between the radially peripheral portions 12B in the second set. Different pulsatile motions can thus be generated simultaneously in conduits 2A, 2B, 6A and 6B. The arrangement may be used in a similar manner to the arrangements described above with reference to FIGS. 11 and 12. Corresponding enhancements in flexibility of operation are provided.

In the embodiments described above the various conduits (e.g. first and second conduits 2 and 6) are shown as individual elements, e.g. lengths of tubing. Structures need to be provided to hold the conduits 2,6 against the rotatable members (e.g. first rotatable member 10) to provide the required engagement between the conduits 2,6 and the radially peripheral portions 12. Further structures allowing connections (e.g. at junction 21) need to be provided. The overall structure required to implement the network of conduits can become mechanically complex, time consuming to assemble and/or take up considerable space.

FIG. 17 depicts an example of an alternative approach, applicable to any of the embodiments discussed above, and other embodiments, in which a conduit support structure 84 defines the first and second conduits 2,6. The conduit support structure 84 may be detachable from the first rotatable member 10. A cut-out portion of the conduit support structure 84 is shown in the right-hand portion of FIG. 17. The cut-out portion corresponds to a portion of the conduit support structure 84 that would be wrapped around the rotatable member 10 in the region of the dot-dash box 82 shown in the left-hand portion of FIG. 17. The conduit support structure 84 may partially or fully wrap around the rotatable member 10 in a circumferential direction. In an embodiment, such as in the example shown in FIG. 17, the conduit support structure 84 comprises lumens that respectively define at least the first and second conduits 2,6. The conduit support structure 84 is continuously integral along at least one path from a lumen defining the first conduit 2 to a lumen defining the second conduit 6. Thus, it is possible in such an embodiment to follow a line through the conduit support structure 84 from at least a portion of the lumen defining the first conduit 2 to at least a portion of the lumen defining the second conduit 6 without passing through any interface, such as an interface between two different types of material or an interface defining where two surfaces have been attached to each other. The conduit support structure 84 allows the conduits (e.g. first and second conduits 2 and 6) to be provided in a single structure, facilitating ease of manufacture and/or handling after manufacture. The conduit support structure 84 also helps to ensure that conduits reliably maintain a desired spatial relationship relative to each other (e.g. angular displacement). The conduit support structure 84 allows the conduits to be formed in a particularly compact manner because the conduit support structure 84 simultaneous defines the conduits and provides a mounting for the conduits. Complex pathways for conduits can easily be manufactured, including conduits that cross over each other and/or otherwise form plural layers in the radial direction.

In an embodiment the conduit support structure 84 further comprises the first junction 21 between the first and second conduits 2,6 (and/or one or more further junctions between other conduits). This approach provides a particularly reliable and compact way of forming junctions between conduits.

In an embodiment, as shown in the example of FIG. 17, the conduit support structure 84 is configured to allow engagement between one or more radially peripheral portions 12 and the first and second conduits while at the same time providing further conduits or junctions which do not engage with the one or more radially peripheral portions 12. In the example of FIG. 17, the further conduits or junctions may be provided within the block of material marked 88 for example.

In other embodiments the conduit support structure may comprise an assembly of plural different elements attached to each other.

The invention claimed is:

1. A method of generating droplets, comprising:
using a pumping mechanism to transport a first fluid in a first conduit; and
using a pumping mechanism to transport a second fluid in a second conduit;
wherein the pumping mechanism comprises a first rotatable member having one or more radially peripheral portions that rotate in unison with each other on rotation of the first rotatable member and engage against the first and second conduits to apply a dynamic deformation to the first and second conduits on rotation of the first rotatable member, the dynamic deformation being such as to drive a pulsatile motion of the first and second fluids in the first and second conduits,
the pulsatile motions of the first and second fluids are phase shifted relative to each other at a first junction between the first and second conduits downstream of the pumping mechanism resulting in the formation of droplets of the second fluid in the first fluid at the first junction;
the first fluid comprises a carrier fluid and the second fluid comprises a sample fluid, the sample fluid being immiscible with the carrier fluid, and either:
the one or more radially peripheral portions comprises a thread winding around the axis of the first rotatable member and the phase shifting of the pulsatile motions of the first and second fluids at the first junction is provided by positioning the first and second conduits at different angular positions around the circumference of the first rotatable member; or
a longitudinal axis of each of the first and second conduits is non-parallel to the axis of rotation of the first rotatable member in a region where the one or more radially peripheral portions engage against the first or second conduit, a set of radially peripheral portions that engage against the first conduit is different from a set of radially peripheral portions that engage against the second conduit, and the phase shifting of the pulsatile motions of the first and second fluids is provided by an angular offset between the set of radially peripheral portions that engage against the first conduit and the set of radially peripheral portions that engage against the second conduit.

2. The method according to claim 1, wherein, in the case where the one or more radially peripheral portions comprises the thread, longitudinal axes of the first and second conduits are parallel to the axis of rotation of the first rotatable member in a region where the one or more radially peripheral portions engage against the first and second conduits.

3. The method according to claim 1, wherein:
the set of radially peripheral portions that engage against the first conduit engage against the first conduit exclusively within a first range of positions along an axis of rotation of the first rotatable member;
the set of radially peripheral portions that engage against the second conduit engage against the second conduit exclusively within a second range of positions along the axis of rotation of the first rotatable member; and
the first range of positions is different to the second range of positions.

4. The method according to claim 1, wherein the pumping mechanism is further used to pump fluid along one or more further conduits, each configured such that the one or more radially peripheral portions engage against each of the one or more further conduits and apply a dynamic deformation to each of the one or more further conduits, on rotation of the first rotatable member, thereby driving a corresponding pulsatile motion of fluid in each of the one or more further conduits.

5. The method according to claim 4, wherein the one or more further conduits are configured such that fluid in these conduits can be driven into the first fluid at the first junction between the first and second conduits in order to form droplets in the first fluid that comprise a mixture of the second fluid and fluid from the one or more further conduits.

6. The method according to claim 4, wherein each of the first, second and one or more further conduits are positioned at different angular positions around the circumference of the first rotatable member.

7. The method according to claim 4, wherein at least one of the one or more further conduits is configured such that fluid in the conduit can be driven into the first fluid at a second junction with the first conduit, the second junction being at a different location to the first junction, thereby allowing droplets of different compositions to be formed in parallel at the first and second junctions.

8. The method according to claim 1, wherein the pumping mechanism comprises one or more further rotatable members configured to be rotated in unison with the first rotatable member.

9. The method according to claim 8, wherein each of the one or more further rotatable members comprises one or more radially peripheral portions that engage against one or more of the following:
   a further instance of the first conduit,
   a further instance of the second conduit, and
   where not previously provided, one or more further conduits, or
   where previously provided, a further instance of the one or more further conduits, wherein
   the one or more radially peripheral portions apply a dynamic deformation to the conduit or conduits with which they engage, on rotation of the rotatable member, thereby driving a corresponding pulsatile motion of fluid in the conduit or conduits with which they engage.

10. The method according to claim 9, wherein at least one of the one or more further rotatable members and corresponding conduits are configured such that a dynamic deformation is applied to at least one of the conduits that has a different form than the dynamic deformation applied by the first rotatable member to the corresponding conduit for the same speed of rotation.

11. The method according to claim 10, wherein the dynamic deformation having a different form results in a pulsatile motion having a different wavelength than the pulsatile motion driven by the first rotatable member for the same speed of rotation.

12. The method according to claim 1, wherein one or more of the radially peripheral portions are configured to engage with at least one of the conduits in such a way that for all angles of rotation of the first rotatable member the at least one conduit is substantially sealed longitudinally by a portion of the one or more radially peripheral portions to prevent backflow in the at least one conduit.

13. The method according to claim 1, wherein one or more of the conduits are detachably connected to the pumping mechanism to allow reuse of the pumping mechanism with different sets of conduits.

14. The method according to claim 1, wherein the pumping mechanism is configured to operate as a peristaltic pump.

15. The method according to claim 1, wherein an output conduit configured to transport the droplets downstream from the first junction, and/or where provided the second junction, is routed such that over a range of positions downstream from the first junction, and/or where provided the second junction, the one or more radially peripheral portions engage against the output conduit and apply a dynamic deformation to the output conduit, on rotation of the first rotatable member, thereby further driving a corresponding pulsatile motion of fluid in the output conduit.

16. The method according to claim 1, wherein a conduit support structure is provided that comprises a lumen defining the first conduit and a lumen defining the second conduit.

17. The method according to claim 16, wherein the conduit support structure is continuously integral along at least one path from the lumen defining the first conduit to the lumen defining the second conduit.

18. The method according to claim 16, wherein the conduit support structure further comprises the first junction between the first and second conduits.

19. A method according to claim 1, wherein the carrier fluid is a hydrophobic fluid and the sample fluid is an aqueous fluid.

20. A method according to claim 1, wherein the sample fluid is a sample taken from a human or animal body.

* * * * *